US010323216B2

(12) United States Patent
Vockenroth et al.

(10) Patent No.: US 10,323,216 B2
(45) Date of Patent: *Jun. 18, 2019

(54) CLEANING AGENT CONTAINING AMYLASES

(71) Applicant: Henkel AG & Co. KGaA, Duesseldorf (DE)

(72) Inventors: Inga Kerstin Vockenroth, Duesseldorf (DE); Thomas Weber, Dormagen (DE); Silke Menke, Haan (DE); Thomas Eiting, Duesseldorf (DE); Nina Mussmann, Willich (DE); Thorsten Bastigkeit, Wuppertal (DE); Noelle Wrubbel, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/322,930

(22) PCT Filed: Jun. 18, 2015

(86) PCT No.: PCT/EP2015/063667

§ 371 (c)(1),
(2) Date: Dec. 29, 2016

(87) PCT Pub. No.: WO2016/000972

PCT Pub. Date: Jan. 7, 2016

(65) Prior Publication Data

US 2017/0152461 A1 Jun. 1, 2017

(30) Foreign Application Priority Data

Jun. 30, 2014 (DE) ........................ 10 2014 212 640

(51) Int. Cl.

| | |
|---|---|
| ***C12N 9/28*** | (2006.01) |
| ***C11D 3/386*** | (2006.01) |
| ***C11D 11/00*** | (2006.01) |
| *C07H 21/04* | (2006.01) |
| *C12N 15/00* | (2006.01) |

(52) U.S. Cl.

CPC .......... *C11D 3/38609* (2013.01); *C11D 3/386* (2013.01); *C11D 11/0023* (2013.01); *C12N 9/2417* (2013.01); *C12Y 302/01001* (2013.01)

(58) Field of Classification Search

None

See application file for complete search history.

(56) References Cited

U.S. PATENT DOCUMENTS

2014/0179585 A1 6/2014 Souter et al.

FOREIGN PATENT DOCUMENTS

| | | | |
|---|---|---|---|
| EP | 2100949 | A1 | 9/2009 |
| WO | 2010090915 | A1 | 8/2010 |

OTHER PUBLICATIONS

Altschul, S.F., et al. "Basic Local Alignment Search Tool," Journal of Molecular Biology, 1990, pp. 403-410, vol. 215.

Altschul, S.F., et al. "Gapped BLAST and PSI-BLAST: a new generation of protein database search programs," Nucleic Acids Research, 1997, pp. 3389-3402, vol. 25, No. 17.

Bender, M.L., et al. "The Determination of the Concentration of Hydrolytic Enzyme Solutions: α-Chymotrypsin, Trypsin, Papain, Elastase, Subtilisi, and Acetylcholinesterase," Journal of the American Chemical Society, Dec. 20, 1966, pp. 5890-5913, vol. 88, No. 24.

EPO, International Preliminary Report on Patentability issued in International Application No. PCT/EP2015/063667, dated Jan. 3, 2017.

EPO, International Search Report and Written Opinion issued in International Application No. PCT/EP2015/063667, dated Aug. 27, 2015.

Preliminary Amendment for U.S. Appl. No. 15/322,953, dated Dec. 29, 2016.

Substitute Specification for U.S. Appl. No. 15/322,953, dated Dec. 29, 2016.

EPO, International Preliminary Report on Patentability issued in International Application No. PCT/EP2015/063668, dated Jan. 3, 2017.

EPO, International Search Report and Written Opinion issued in International Application No. PCT/EP2015/063668, dated Aug. 31, 2015.

*Primary Examiner* — Yong D Pak

(74) *Attorney, Agent, or Firm* — LORENZ & KOPF, LLP

(57) ABSTRACT

A cleaning agent for hard surfaces and methods for cleaning are provided herein. In one embodiment, the cleaning agent includes at least one first amylase, wherein the first amylase is an α-amylase from *Bacillus* sp. No. 707 or a functional fragment or a variant thereof. The cleaning agent further includes at least one second amylase, wherein the second amylase is an AA560 α-amylase from *Bacillus* sp. or a functional fragment or a variant thereof. In another embodiment, the method includes dispensing the cleaning agent into the interior of an automatic dishwasher while a dishwashing program is being executed, before the main washing cycle begins, or in the course of the main washing cycle.

20 Claims, No Drawings

Specification includes a Sequence Listing.

CLEANING AGENT CONTAINING AMYLASES

CROSS-REFERENCE TO RELATED APPLICATION

This application is a U.S. National-Stage entry under 35 U.S.C. § 371 based on International Application No. PCT/EP2015/063667, filed Jun. 18, 2015 which was published under PCT Article 21(2) and which claims priority to German Application No. 10 2014 212 640.1, filed Jun. 30, 2014, which are all hereby incorporated in their entirety by reference.

TECHNICAL FIELD

The present application is directed to a cleaning agent, preferably a dishwashing agent, especially an automatic dishwashing agent, which comprises at least two amylases, and to the use of such a cleaning agent.

BACKGROUND

The most important criterion when cleaning textiles, hard surfaces, such as in particular when washing dishes, in particular during automatic dish washing, is the cleaning performance when it comes to a wide variety of soiling, which is introduced in particular in the form of food residue. While the cleaning performance of dishwashing agents used today is generally high, the problem that arises, among other things due to the general trend in automatic dishwashing to increasingly use low-temperature programs, is that many of the usual automatic dishwashing agents exhibit inadequate cleaning performance on stubborn soiling. Such inadequate cleaning performance and the attendant inadequate cleaning of the dishes result in dissatisfaction on the part of the consumer and in the consumer pretreating such soiling, which in turn increases the consumption of water and energy. As a result, a general need exists for automatic dishwashing agents that exhibit good cleaning performance even on stubborn, in particular burn-on, soiling, without reducing the existing good cleaning performance when it comes to other types of soiling.

BRIEF SUMMARY

A cleaning agent for hard surfaces and methods for cleaning are provided herein. In one embodiment, the cleaning agent includes at least one first amylase, wherein the first amylase is an α-amylase from *Bacillus* sp. No. 707 or a functional fragment or a variant thereof. The cleaning agent further includes at least one second amylase, wherein the second amylase is an AA560 α-amylase from *Bacillus* sp. or a functional fragment or a variant thereof.

In another embodiment, the method includes dispensing the cleaning agent into the interior of an automatic dishwasher while a dishwashing program is being executed, before the main washing cycle begins, or in the course of the main washing cycle.

DETAILED DESCRIPTION

The following detailed description is merely exemplary in nature and is not intended to limit the invention or the application and uses of the invention. Furthermore, there is not intention to be bound by any theory presented in the preceding background or the following detained description.

It was therefore the object of the present disclosure to provide a cleaning agent, preferably a dishwashing agent, especially an automatic dishwashing agent, which exhibits enhanced cleaning performance of such soiling, without the cleaning performance being reduced when it comes to other types of soiling.

Surprisingly, it has now been established that the use of a combination of different amylases improves the cleaning performance of corresponding cleaning agents, preferably of a dishwashing agent, especially an automatic dishwashing agent, when it comes to enzyme-sensitive soiling, in particular burnt-on food soiling.

In a first aspect, the present disclosure is thus directed to a cleaning agent (for hard surfaces), in particular a dishwashing agent, especially an automatic dishwashing agent, which comprises a first amylase and a second amylase, wherein a) the first amylase is an α-amylase from *Bacillus* sp. No. 707 or a functional fragment or a variant thereof;

b) the second amylase is an AA560 α-amylase from *Bacillus* sp. or a functional fragment or a variant thereof.

When using the agent, such a combination of multiple amylases results in significantly enhanced cleaning performance when it comes to stubborn soiling, in particular starch-containing soiling.

A further object of the present disclosure is the use of a cleaning described herein, preferably a dishwashing agent, especially an automatic dishwashing agent, in a cleaning method, preferably a dishwashing method, especially in an automatic dishwashing method, preferably the use for improving the cleaning performance, in particular the cleaning performance when it comes to enzyme-sensitive soiling on hard surfaces, in particular dishes when cleaning the same, preferably in an automatic dishwasher, in particular stubborn soiling, among other things also at temperatures that are lower than the customarily used temperatures.

A further object of the present disclosure is a cleaning method, preferably a dishwashing method, especially an automatic dishwashing method, in which a cleaning agent described herein, preferably a dishwashing agent, especially an automatic dishwashing agent, is used in particular for the purpose of improving the cleaning performance when it comes to enzyme-sensitive soiling. In various embodiments of the disclosure, temperatures that are lower than the customarily used temperatures are used in the dishwashing method.

Still another object of the disclosure is the use of the enzyme combinations described herein to improve the cleaning performance of a cleaning agent, in particular of a dishwashing agent.

"Low temperatures" or "temperatures that are lower than the customarily used temperatures," as used herein in the context of dishwashing methods, preferably refers to temperatures below 60° C., in particular below 55° C., still more preferably 50° C. or lower, particularly preferably 45° C. or lower, and most preferably 40° C. or lower. This temperature information refers to the target temperatures (maximum temperatures) used in the cleaning steps.

These and further aspects, features and advantages of the disclosure become apparent to a person skilled in the art when studying the following detailed description and claims. Every feature from one aspect of the disclosure may be used in another aspect of the disclosure. Moreover, it goes without saying that the examples contained herein are intended to describe and illustrate the disclosure, but do not limit the same, and in particular the disclosure is not limited to these examples. All percentage information is percent by weight, unless indicated otherwise. Numerical ranges indicated in the format "from x to y" include the mentioned values. If several preferred numerical ranges are indicated in this format, it goes without saying that all ranges resulting from the combination of the different end points are likewise covered.

The amylases used are alkaline α-amylases. They act as hydrolases and cleave the =-(1-4) glycosidic bond of polysaccharides, in particular starches such as amylose, and thereby bring about the decomposition of starch-containing soiling on the goods to be cleaned. Cleavage products that result are dextrins, and maltose, glucose and branched oligosaccharides therefrom. The pH optimum of these is usually in the distinctly alkaline range.

The wild type sequences of the mature α-amylase from *Bacillus* sp. No. 707 and of the mature AA560 α-amylase from *Bacillus* sp. are indicated in SEQ ID NO. 1 and SEQ ID NO. 2, respectively.

"Different," as used herein with respect to the enzymes, refers to enzymes that differ in terms of the amino acid sequence thereof. In various embodiments, enzymes that are different from each other originate from different types of organisms or differ from each other by mutations, for example those created artificially.

"Variant," as used herein in the context of enzymes, refers to natural or artificially created variations of a native enzyme which have an amino acid sequence that is modified compared to the reference form. Such a variant may have single or multiple point mutations, which is to say substitutions of one amino acid naturally occurring at the corresponding position by another, insertions (introduction of one or more amino acids) and/or deletions (removal of one or more amino acids), in particular one or more point mutations. Such variants preferably have at least 50%, preferably 60% or more, still more preferably 70%, 80%, 90%, 100% or more of the enzyme activity of the reference form. In various embodiments, such a variant has an amino acid sequence that is at least 70%, preferably 75%, 80%, 85%, 90%, 95%, 96%, 97%, 98% or 99% identical to the sequence serving as the reference across the total length thereof. The variants preferably have the same length as the reference sequence. Variants may stand out compared to the reference form by improved properties, such as higher enzyme activity, higher stability, changed substrate specificity, and the like. Only variants exhibiting enzymatic activity are used. "Enzymatic activity," as used in this context, means in particular that the corresponding enzymes exhibit at least 50%, preferably at least 90% of the catalytic activity of the reference enzyme thereof.

"Fragment," as used herein in the context of enzymes, refers to polypeptides that, at the N-terminal end and/or C-terminal end, are shorted by one or more amino acids in relation to the reference enzyme. Only fragments exhibiting enzymatic activity are used. "Enzymatic activity," as used in this context, means in particular that the corresponding enzymes exhibit at least 50%, preferably at least 90% of the catalytic activity of the reference enzyme thereof.

The identity of nucleic acid or amino acid sequences is determined by way of a sequence comparison. This sequence comparison is based on the BLAST algorithm that is established in the prior art and customarily used (see, for example, Altschul, S. F., Gish, W., Miller, W., Myers, E. W. & Lipman, D. J. (1990) "Basic local alignment search tool." J. Mol. Biol. 215:403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, pgs. 3389-3402) and is essentially carried out by assigning similar successions of nucleotides or amino acids in the nucleic acid sequences or amino acid sequences to each other. A tabular assignment of the particular positions is referred to as an alignment. Another algorithm available in the prior art is the FASTA algorithm.

Such a comparison also allows information to be provided about the similarity of the compared sequences among each other. It is customarily indicated in percent identity, which is to say the proportion of identical nucleotides or amino acid residues at the same positions or at positions corresponding to each other in an alignment. The broader concept of homology, in the case of amino acid sequences, takes conserved amino acid exchanges into consideration, which is to say amino acids having similar chemical activity, since these generally carry out similar chemical activities within the protein. The similarity of the compared sequences may thus also be indicated in percent homology or percent similarity. Identity and/or homology information can be provided for entire polypeptides or genes, or only for individual regions. Homologous or identical regions of different nucleic acid or amino acid sequences are therefore defined by agreement in the sequences. Such regions often have identical functions. They may be small and comprise only few nucleotides or amino acids. Such small regions often carry out functions that are essential for the overall activity of the protein. It may therefore be useful to relate sequence agreements only to individual, optionally small regions. Unless indicated otherwise, however, identity or homology information in the present application refers to the total length of the respective indicated nucleic acid sequence or amino acid sequence.

In various preferred embodiments, the first amylase used within the meaning of the present disclosure is an amylase that includes an amino acid sequence that is at least 80% identical to the amino acid sequence indicated in SEQ ID NO. 1 over the total length thereof and optionally has at least one amino acid substitution at one of the positions 172, 202, 208, 255 and 261 in the count according to SEQ ID NO. 1, in particular selected from the group consisting of M202L, M202V, M202S, M202T, M202I, M202Q, M202W, S255N and R172Q.

In preferred embodiments of the disclosure, the first amylase used is thus a variant of the α-amylase from *Bacillus* sp. No. 707 including the amino acid sequence indicated in SEQ ID NO. 1, which is at least 80% identical to the amino acid sequence indicated in SEQ ID NO. 1 over the total length thereof and has at least one amino acid substitution at one of the positions 172, 202, 208, 255 and 261 in the count according to SEQ ID NO. 1. Preferably, amylases are used which at two, preferably three, of the above-described positions have an amino acid substitution, in particular a substitution at position 202 selected from M202L, M202V, M202S, M202T, M202I, M202Q, M202W, a substitution at position 255, in particular S255N, and a substitution at position 172, in particular R172Q. The M202L and M202T mutants are especially particularly preferred.

Further variants that may be used are those including an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence indicated in SEQ ID NO. 1, wherein positions 172, 202 and 255 are preferably substituted as described above. Such variants may include a shortening of the C-terminus, for example, such as by 1 to 20 amino acids, or a deletion of one or more amino acids, in particular at positions 181, 182, 183 and 184 in the count according to SEQ ID NO. 1, wherein, however, the enzymatic activity is maintained, which is to say the activity of the variant is at least 60% of the activity of the enzyme including the amino acid sequence of SEQ ID NO. 1. Suitable amylases are also described in WO 2008/112459 A2, the entire disclosure of which is hereby incorporated by reference.

The second amylase is different from the first amylase, which is to say an amylase that is covered both by the definition of the first amylase and that of the second amylase cannot simultaneously be considered a first amylase and a second amylase.

In various embodiments of the disclosure, the second amylase includes an amino acid sequence that is at least 80% identical to the amino acid sequence indicated in SEQ ID NO. 2 over the entire length thereof, and optionally has at least one amino acid substitution at one of positions 9, 26, 30, 33, 82, 37, 106, 118, 128, 133, 149, 150, 160, 178, 182, 186, 193, 195, 202, 203, 214, 231, 256, 257, 258, 269, 270, 272, 283, 295, 296, 298, 299, 303, 304, 305, 311, 314, 315, 318, 319, 320, 323, 339, 345, 361, 378, 383, 419, 421, 437, 441, 444, 445, 446, 447, 450, 458, 461, 471, 482 and 484 and/or one of the deletions D183* and G184* in the count according to SEQ ID NO. 2.

In various preferred embodiments, the second amylase, in the count according to SEQ ID NO. 2, includes amino acid substitutions at three or more of positions 9, 26, 149, 182, 186, 202, 257, 295, 299, 323, 339 and 345 and optionally has one or more, preferably all, of the substitutions and/or deletions at positions 118, 183, 184, 195, 320 and 458, particularly preferably R118K, D183*, G184*, N195F, R320K and/or R458K.

In particularly preferred embodiments, the second amylase includes the following amino acid substitutions and/or deletions in the count according to SEQ ID NO. 2:

(i) M9L+M323T;

(ii) M9L+M202L/T/V/I+M323T;

(iii) M9L+N195F+M202L/T/V/I+M323T;

(iv) M9L+R118K+D183*+G184*+R320K+M323T+R458K;

(v) M9L+R118K+D183*+G184*+M202L/T/V/I+R320K+M323T+R458K;

(vi) M9L+G149A+G182T+G186A+M202L+T257I+Y295F+N299Y+M323T+A339S+E345R;

(vii) M9L+G149A+G182T+G186A+M202I+T257I+Y295F+N299Y+M323T+A339S+E345R;

(viii) M9L+R118K+G149A+G182T+D183*+G184*+G186A+M202L+T257I+Y295F+N299Y+R320K+M323T+A339S+E345R+R458K;

(ix) M9L+R118K+G149A+G182T+D183*+G184*+G186A+N195F+M202L+T257I+Y295F+N299Y+R320K+M323T+A339S+E345R+R458K;

(x) M9L+R118K+G149A+G182T+D183*+G184*+G186A+M202I+T257I+Y295F+N299Y+R320K+M323T+A339S+E345R+R458K;

(xi) M9L+R118K+D183*+D184*+N195F+M202L+R320K+M323T+R458K;

(xii) M9L+R118K+D183*+D184*+N195F+M202T+R320K+M323T+R458K;

(xiii) M9L+R118K+D183*+D184*+N195F+M202I+R320K+M323T+R458K;

(xiv) M9L+R118K+D183*+D184*+N195F+M202V+R320K+M323T+R458K;

(xv) M9L+R118K+N150H+D183+D184*+N195F+M202L+V214T+R320K+M323T+R458K; or (xvi) M9L+R118K+D183*+D184*+N195F+M202L+V214T+R320K+M323T+E345N+R458K.

A particularly preferred second amylase is a variant that is commercially available by the trade name Stainzyme Plus™ (Novozymes A/S, Bagsvaerd, Denmark).

Preferred within the scope of the present disclosure are combinations of a first amylase, which is at least 80% identical to the amino acid sequence indicated in SEQ ID NO. 1 over the total length thereof and has at least one amino acid substitution at one of positions 172, 202, 208, 255 and 261 in the count according to SEQ ID NO. 1, in particular a substitution at position 202 selected from M202L, M202V, M202S, M202T, M202I, M202Q, M202W, a substitution at position 255, in particular S255N, and a substitution at position 172, in particular R172Q, and a second amylase, which is at least 80% identical to the amino acid sequence indicated in SEQ ID NO. 2 over the total length thereof and includes the following amino acid substitutions and/or deletions:

(i) M9L+M323T;

(ii) M9L+M202L/T/V/I+M323T;

(iii) M9L+N195F+M202L/T/V/I+M323T;

(iv) M9L+R118K+D183*+G184*+R320K+M323T+R458K;

(v) M9L+R118K+D183*+G184*+M202L/T/V/I+R320K+M323T+R458K;

(vi) M9L+G149A+G182T+G186A+M202L+T257I+Y295F+N299Y+M323T+A339S+E345R;

(vii) M9L+G149A+G182T+G186A+M202I+T257I+Y295F+N299Y+M323T+A339S+E345R;

(viii) M9L+R118K+G149A+G182T+D183*+G184*+G186A+M202L+T257I+Y295F+N299Y+R320K+M323T+A339S+E345R+R458K;

(ix) M9L+R118K+G149A+G182T+D183*+G184*+G186A+N195F+M202L+T257I+Y295F+N299Y+R320K+M323T+A339S+E345R+R458K;

(x) M9L+R118K+G149A+G182T+D183*+G184*+G186A+M202I+T257I+Y295F+N299Y+R320K+M323T+A339S+E345R+R458K;

(xi) M9L+R118K+D183*+D184*+N195F+M202L+R320K+M323T+R458K;

(xii) M9L+R118K+D183*+D184*+N195F+M202T+R320K+M323T+R458K;

(xiii) M9L+R118K+D183*+D184*+N195F+M202I+R320K+M323T+R458K;

(xiv) M9L+R118K+D183*+D184*+N195F+M202V+R320K+M323T+R458K;

(xv) M9L+R118K+N150H+D183*+D184*+N195F+M202L+V214T+R320K+M323T+R458K; or (xvi) M9L+R118K+D183*+D184*+N195F+M202L+V214T+R320K+M323T+E345N+R458K.

In various embodiments, these combinations of amylases are used in a mass ratio of 50:1 to 1:50, preferably 30:1 to 1:10 (in each case based on the amount of active protein amylase 1 to amylase 2).

It is particularly preferred to use an amylase according to 1) in relation to an amylase according to 2) at a ratio of about 20:1 to about 2:1, preferably about 15:1 to about 3:1, and particularly preferably 12:1 to 5:1, for example 10:1. In particular, it is most preferred in this context to use one of the above-described variants i) to xvi) of SEQ ID NO. 1 as the first amylase, and one of the above-described variants i) to xvi) of SEQ ID NO. 2 as the second amylase at a ratio of about 15:1 to about 3:1, and particularly preferably about 12:1 to about 5:1, for example 10:1.

In preferred embodiments, the cleaning agents described herein can furthermore contain at least one protease, and in particular at least one first protease and at least one second protease.

The proteases are in particular alkaline serine proteases. They act as non-specific endopeptidases, which is to say they hydrolyze arbitrary acid amide bonds that lie in the interior of peptides or proteins, thereby causing the decomposition of protein-containing soiling on the goods to be cleaned. The pH optimum of these is usually in the distinctly alkaline range.

The at least one protease is preferably selected from the group consisting of a subtilisin 309 from *Bacillus lentus* or a functional fragment or a variant thereof, and an alkaline protease from *Bacillus lentus* DSM 5483 or a functional fragment or a variant thereof. Likewise, it is possible to use combinations of several of the above-mentioned enzymes.

The sequences of the mature protease subtilisin 309 from *Bacillus lentus* and of the mature alkaline protease from *Bacillus lentus* DSM 5483 are indicated in SEQ ID NO. 3 and SEQ ID NO. 4, respectively.

In various embodiments of the disclosure, the at least one protease comprises a subtilisin 309 from *Bacillus lentus* or a functional fragment or a variant thereof, including an amino acid sequence that is at least 80% identical, preferably at least 90% identical, and in particular 100% identical to the amino acid sequence indicated in SEQ ID NO. 3 over the total length thereof and has at least one amino acid substitution at one of positions 9, 15, 66, 212 and 239 in the count according to SEQ ID NO. 3. Preferred are those which have an amino acid substitution at two, preferably three, in particular four, most particularly preferably five of the above-mentioned positions.

Further variants that may be used are those including an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence indicated in SEQ ID NO. 3, wherein one or more of positions 9, 15, 66, 212 and 239 are substituted, which is to say the amino acid at these positions does not correspond to the corresponding amino acid in SEQ ID NO. 3.

Particularly preferably a variant including at least one, preferably two, in particular three, particularly preferably four, or most particularly preferably 5 of the amino acid substitutions selected from S9R, A15T, V66A, N212D and Q239R, based on the count according to SEQ ID NO. 3, is used. Preferred are the following combinations: S9R+V66A+N212D+Q239R, S9R+A15T+N212D+Q239R, S9R+A15T+V66A+Q239R, S9R+A15T+V66A+N212D, A15T+V66A+N212D+Q239R; S9R+A15T+V66A, S9R+A15T+N212D, S9R+A15T+Q239R, S9R+N212D+Q239R, S9R+V66A+N212D, S9R+V66A+Q239R, A15T+V66A+N212D, A15T+V66A+Q239R, A15T+N212D+Q239R, V66A+N212D+Q239R; S9R+A15T, S9R+V66A, S9R+N212D, S9R+Q239R, A15T+V66A, A15T+N212D, A15T+Q239R, V66A+N212D, V66A+Q239R, N212D+Q239R. One variant that covers all of the above-described modification has the amino acid sequence indicated in SEQ ID NO. 5 (S9R+A15T+V66A+N212D+Q239R).

Likewise particularly preferred are variants of the protease including the amino acid sequence indicated in SEQ ID NO. 3, which comprises an amino acid substitution at position 99 and an insertion of one amino acid between the amino acids at positions 99 and 100 in the count according to SEQ ID NO. 3, preferably selected from SA99A and/or S99_G100InsD. Further variants that may be used are those including an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence indicated in SEQ ID NO. 3, wherein these variants include one or both of the above-described mutations at positions 99 and 100. Preferred are those that comprise both mutations. Such a variant has the amino acid sequence indicated in SEQ ID NO. 6.

In various, still further embodiments of the disclosure, the at least one protease comprises an alkaline protease from *Bacillus lentus* DSM 5483 or a functional fragment or a variant thereof, which includes an amino acid sequence that is at least 80% identical, preferably at least 90% identical, and in particular 100% identical to the amino acid sequence indicated in SEQ ID NO. 4 over the total length thereof and that optionally has at least one amino acid substitution at one, two, three or four of the following positions: 3, 4, 99 and 199 in the count according to SEQ ID NO. 4. Preferably proteases are used which have an amino acid substitution at two, preferably three or more, in particular four of the above-mentioned positions.

Further variants that may be used are those which include an amino acid sequence that is at least 81%, 82%, 83%, 84%, 85%, 86%, 87%, 88%, 89%, 90%, 91%, 92%, 93%, 94%, 95%, 96%, 97%, 98% or 99% identical to the amino acid sequence indicated in SEQ ID NO. 4, and comprise at least one amino acid substitution at one of the following positions: 3, 4, 99 and 199.

Particularly preferably, such a protease includes an amino acid sequence that is at least 80% identical to the amino acid sequence indicated in SEQ ID NO. 4 over the total length thereof and has the amino acid substitution R99E or R99D in the count according to SEQ ID NO. 4, and optionally additionally at least one or two, and preferably all three of the amino acid substitutions S3T, V4I and V199I.

Such a protease preferably includes an amino acid sequence that, in the count according to SEQ ID NO. 4, comprises at least one, preferably more, in particular each of the following amino acid substitutions R99E/R99D, S3T, V4I and/or V199I and at all other positions is at least 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 99%, and in particular 100%, identical to the amino acid sequence indicated in SEQ ID NO. 4 over the entire length thereof. Particularly preferred is a protease that includes an amino acid sequence that, proceeding from the amino acid sequence having the SEQ ID NO. 4, can be obtained by one or more of the amino acid substitutions R99E/R99D, S3T, V4I and/or V199I according to the count according to SEQ ID NO. 4. Such a protease can include the amino acid sequence indicated in one of SEQ ID NOs. 7 to 8.

It is particularly preferred as contemplated herein to use a combination of a first protease and a second protease. The first protease used is in particular a variant of the protease including the amino acid sequence according to SEQ ID NO. 3, preferably a variant as described above that comprises at least one amino acid substitution at one of positions 9, 15, 66, 212 and 239 in the count according to SEQ ID NO. 3. In one embodiment, this first protease is at least 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence indicated in SEQ ID NO. 3 over the entire length thereof and comprises four, and especially particularly preferably 5 of the amino acid substitutions selected from S9R, A15T, V66A, N212D and Q239R based on the count according to SEQ ID NO. 3. The first protease is especially particularly preferably a protease including the amino acid sequence according to SEQ ID NO. 5.

The second protease is selected from the remaining that are described above. Preferred combinations are those of the protease having the SEQ ID NO. 5 with one of the proteases including the amino acid sequences according to SEQ ID NOs. 6 to 8.

In different embodiments, combinations of two proteases are used at a mass ratio of about 10:1 to about 1:10, preferably about 5:1 to about 1:5, and in particular about 3:1 to about 1:1, for example 2:1, in each case based on active protein.

Surprisingly, the combinations of different amylases, and optionally also proteases, described herein have the property to improve the performance of the cleaning agent, preferably of the dishwashing agent, by resulting in improved cleaning performance when it comes to stubborn, such as burnt-on, soiling. The increase in cleaning performance can also be observed at low temperatures, which is to say temperatures that are lower than those customarily used in dishwashing methods, as defined above. This makes it possible to carry out the cleaning method, preferably the automatic dishwashing method, at lower temperatures and nonetheless preserve the good cleaning performance.

The improvement in cleaning performance shall in general be understood to mean that the removal of soiling, in particular burnt-on soiling, from hard surfaces, in particular dishes, is noticeably improved when using the cleaning agents described herein, and in particular the dishwashing agents, for cleaning these dishes, preferably in an automatic dishwasher, compared to the use of cleaning agents, preferably dishwashing agents, that do not contain the enzyme combinations described herein.

The enzymes to be used can furthermore be formulated together with by-products, such as from fermentation, or with stabilizers.

The cleaning agents, in particular dishwashing agents, preferably contain each amylase, and optionally also each protease, in a quantity of the respective active protein from about $1\times10^{-8}$ to 5 wt. %, based on the total weight of the agent. Preferably about 0.001 to about 2 wt. %, more preferably about 0.005 to about 1.5 wt. %, still more preferably about 0.0075 to about 1 wt. %, and particularly preferably 0.01 to 0.6 wt. % active protein of each enzyme is preferably present in these agents.

In particularly preferred embodiments, the first amylase is used in the agents described herein in a total quantity of the active protein from about 0.01 to about 1 wt. %, preferably about 0.025 to about 0.6 wt. %, based on the total weight of the cleaning agent. Similarly, the second amylase is preferably used in a total quantity of the active protein from about 0.005 to about 0.6 wt. %, preferably about 0.0075 to about 0.2 wt. %.

The first amylase used is preferably about 0.01 to about 1 wt. %, especially about 0.025 to about 0.6 wt. % of an amylase that comprises an amino acid sequence that is at least 80% identical to the amino acid sequence indicated in SEQ ID NO. 1 over the entire length thereof and optionally has at least one amino acid substitution at one of positions 172, 202, 208, 255 and 261 in the count according to SEQ ID NO. 1, in particular selected from the group consisting of M202L, M202V, M202S, M202T, M202I, M202Q, M202W, S255N and R172Q, and the second amylase used is 0.005 to 0.6 wt. %, especially 0.0075 to 0.2 wt. % of an amylase that comprises an amino acid sequence that is at least 80% identical to an amino acid sequence indicated in SEQ ID NO. 2 over the entire length thereof and, in the count according to SEQ ID NO. 2, includes amino acid substitutions at three or more of positions 9, 26, 149, 182, 186, 202, 257, 295, 299, 323, 339 and 345 and optionally has one or more, preferably all, of the substitutions and/or deletions at positions 118, 183, 184, 195, 320 and 458, particularly preferably R118K, D183*, G184*, N195F, R320K and/or R458K, and at all other positions is 100% identical to the amino acid sequence indicated in SEQ ID NO. 2 over the entire length thereof.

In the above-described combination of first and second amylases, preferably furthermore at least one protease is used, and still more preferably a first protease and a second protease. The first protease used is in particular a variant of the protease including the amino acid sequence according to SEQ ID NO. 3, preferably a variant as described above that comprises at least one amino acid substitution at one of positions 9, 15, 66, 212 and 239 in the count according to SEQ ID NO. 3. In one embodiment, this first protease is at least 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence indicated in SEQ ID NO. 3 over the entire length thereof and comprises four, or especially particularly preferably 5 of the amino acid substitutions selected from S9R, A15T, V66A, N212D and Q239R based on the count according to SEQ ID NO. 3. The first protease is especially particularly preferably a protease including the amino acid sequence according to SEQ ID NO. 5.

If a second protease is also present, this is preferably selected from the proteases including the amino acid sequences indicated in SEQ ID NOs. 6 to 8.

In liquid formulations, the enzymes are preferably used in the form of liquid enzyme formulation(s).

The protein concentration can be determined using known methods, such as the BCA method (bicinchoninic acid; 2,2'-bichinolyl-4,4'-dicarbonic acid) or the biuret method. The active protein concentration is determined in this regard by a titration of the active centers using a suitable irreversible inhibitor (for proteases, for example, phenylmethylsulfonyl fluoride (PMSF)) and determination of the residual activity (see M. Bender et al., J. Am. Chem. Soc. 88, 24 (1966), pgs. 5890-5913).

Enzymes, and in particular the amylases and proteases described herein, can be protected in particular during storage against damage, such as inactivation, denaturing or disintegration, for example due to physical influences, oxidation or proteolytic cleavage. Inhibiting proteolysis is particularly preferred in the case of microbial production. The described agents may contain stabilizers for this purpose.

Enzymes with cleaning action are generally not provided in form of the pure protein, but rather in the form of stabilized, storable and transportable preparations. These preformulated preparations include, for example, solid preparations obtained by way of granulation, extrusion or lyophilization or, in particular in the case of liquid or gel-like agents, solutions of the enzymes, advantageously concentrated to the extent possible, low-hydrate and/or mixed with stabilizers or other auxiliary agents.

Alternatively, the enzymes can be encapsulated, both for the solid and the liquid packaging format, for example by spray drying or extruding the enzyme solution together with a preferably natural polymer, or in the form of capsules, for example those in which the enzymes are enclosed as in a solidified gel, or in those of the core-shell type, in which an enzyme-containing core is coated with a protective layer impervious to water, air and/or chemicals. Additional active substances, such as stabilizers, emulsifiers, pigments, bleaching agents or dyes can additionally be applied in superimposed layers. Such capsules are applied using methods that are known per se, for example agitation or roll granulation, or in fluid bed processes. Such granules are advantageously low-dust, for example by applying polymeric film formers, and storage-stable due to the coating.

It is furthermore possible to formulate two or more enzymes together, so that individual granules have multiple enzyme activities.

As is apparent from the comments above, the enzyme protein forms only a fraction of the total weight of customary enzyme preparations. Preferably used enzyme preparations contain between about 0.1 and about 40 wt. %, preferably between about 0.2 and about 30 wt. %, particularly preferably between about 0.4 and about 20 wt. %, and in particular between about 0.8 and about 15 wt. % of the enzyme protein. The described agents thus preferably comprise such enzyme preparations in each case in quantities from about 0.1 to about 10 wt. %, preferably about 0.2 to about 5 wt. %, based on the total agent.

The cleaning agents described herein, in particular the preferred automatic dishwashing agents, can be of a solid or liquid nature, and in particular be present as powdery solids, in post-compacted particle form, as homogeneous solutions or suspensions. In a further preferred embodiment of the disclosure, the automatic dishwashing agent is present in preportioned form. In a further preferred embodiment of the disclosure, the automatic dishwashing agent comprises multiple compositions that are physically separated from each other, whereby it is possible to separate incompatible ingredients from each other, or to offer compositions in combinations which are used at different points in time in the dishwasher. This is particularly advantageous when the automatic dishwashing agents are present in preportioned form. At least one of the compositions may be present in solid form and/or at least one of the compositions may be present in liquid form, wherein the amylases and optionally also the proteases are present in at least one of the compositions, but may also be present in multiple compositions.

The agents described herein preferably comprise at least one further component, in particular at least two further components, selected from the group consisting of builders, surfactants, polymers, bleaching agents, bleach catalysts, bleach activators, non-protease and non-amylase enzymes, corrosion inhibitors and glass corrosion inhibitors, disintegrants, odorants and perfume carriers.

Possible ingredients are described hereafter, which can advantageously be used in the cleaning agents described herein, in particular dishwashing agents, preferably automatic dishwashing agents.

Advantageously, builders may be used. The builders include in particular zeolites, silicates, carbonates, organic cobuilders and—where ecological bias against their use is absent—also phosphates.

Crystalline phyllosilicates may be used in the agents described herein. Such cleaning agents, preferably dishwashing agents, in particular automatic dishwashing agents, preferably contain a weight fraction of crystalline phyllosilicate from about 0.1 to about 20 wt. %, preferably from about 0.2 to about 15 wt. %, and in particular from about 0.4 to about 10 wt. %, in each case based on the total weight of these agents.

It is also possible to use the generally known phosphates as builder substances, provided that such use should not be avoided for ecological reasons. Among the plurality of commercially available phosphates, alkali metal phosphates have the greatest significance in the laundry detergent or cleaning agent industry, pentasodium and pentapotassium triphosphate (sodium or potassium tripolyphosphate) being particularly preferred.

Alkali metal phosphates is the term that covers all the alkali metal (in particular sodium and potassium) salts of the different phosphoric acids, in which a distinction can be made between metaphosphoric acids $(HPO_3)_n$ and orthophosphoric acid $H_3PO_4$, in addition to higher molecular weight representatives. The phosphates combine several advantages: They act as alkali carriers, prevent limescale deposits on machine parts or lime scaling on woven fabrics, and additionally contribute to the cleaning performance.

Technically particularly important phosphates are pentasodium triphosphate, $Na_5P_3O_{10}$ (sodium tripolyphosphate), and the corresponding potassium salt pentapotassium triphosphate, $K_5P_3O_{10}$ (potassium tripolyphosphate). The sodium potassium tripolyphosphates are preferably used.

If within the scope of the present application phosphates are used as substances with washing or cleaning action in the cleaning agents, preferably dishwashing agents, in particular in the automatic dishwashing agents, preferred agents comprise this (these) phosphate(s), preferably alkali metal phosphate(s), particularly preferably pentasodium or pentapotassium triphosphate (sodium or potassium tripolyphosphate), in quantities from about 5 to about 80 wt. %, preferably from about 15 to about 75 wt. %, and in particular from about 20 to about 70 wt. %, in each case based on the weight of the cleaning agent, preferably dishwashing agent, in particular automatic dishwashing agent. However, it is preferred that the cleaning agents described herein are essentially free of phosphates, and in particular the above-described phosphates.

"Phosphate-free," as used herein, means that the composition in question is essentially free of phosphates, which is to say in particular comprises phosphates in amounts of less than 0.1 wt. %, preferably less than 0.01 wt. %, based on the total composition. If phosphates are nonetheless present, these are preferably used in amounts that correspond to no more than 0.3 g/job. The expression g per job (g/job) or g/application refers to the amount of active substance used in relation to the total weight of the agent used for a complete cleaning cycle (which is to say in the case of automatic dishwashing agents, the total amount of the cleaning agent used in a complete cleaning cycle of a dishwasher). In the case of preportioned cleaning agents (preferably automatic dishwashing agents), this information is the amount of the active substance in g based on the total weight of the preportioned cleaning agent. The expression "phosphates", as used in this context, does not include the phosphonates described hereafter.

Other builders are the alkali carriers. For example, alkali metal hydroxides, alkali metal carbonates, alkali metal hydrogen carbonates, alkali metal sesquicarbonates, the described alkali silicates, alkali metal silicates and mixtures of the above-mentioned substances are considered alkali carriers, wherein within the meaning of the present disclosure preferably the alkali carbonates, in particular sodium carbonate, sodium hydrogen carbonate or sodium sesquicarbonate, can be used. A builder system containing a mixture of tripolyphosphate and sodium carbonate is particularly preferred. A builder system containing a mixture of tripolyphosphate and sodium carbonate and sodium silicate is likewise particularly preferred. Due to the low chemical compatibility of the optional alkali metal hydroxides with the remaining ingredients of cleaning agents, in particular dishwashing agents, preferably automatic dishwashing agents, compared to other builder substances, they are preferably used only in small quantities or not at all.

The use of carbonate(s) and/or hydrogen carbonate(s), preferably alkali carbonate(s), particularly preferably sodium carbonate, in quantities from about 2 to about 50 wt. %, preferably from about 5 to about 40 wt. %, and in particular from about 7.5 to about 30 wt. %, in each case based on the weight of the agent, preferably automatic dishwashing agent, is particularly preferred. Agents that, based on the weight of the automatic dishwashing agent, contain less than 20 wt. %, especially less than 17 wt. %, preferably less than 13 wt. %, and in particular less than 9 wt. % carbonate(s) and/or hydrogen carbonate(s), preferably alkali carbonate(s), particularly preferably sodium carbonate, are particularly preferred.

In particular, polycarboxylates/polycarboxylic acids, polymeric polycarboxylates, aspartic acid, polyacetals, dextrins, further organic cobuilders and phosphonates shall be mentioned as organic cobuilders. These substance classes are described hereafter.

Usable organic builder substances are, for example, the polycarboxylic acids that can be used in the form of the free acid and/or of the sodium salts thereof, wherein polycarboxylic acids shall be understood to mean those carboxylic acids that carry more than one acid function. These include, for example, citric acid, adipic acid, succinic acid, glutaric acid, malic acid, tartaric acid, maleic acid, fumaric acid, saccharic acids, nitrilotriacetic acid (NTA), provided that such use is not objectionable for ecological reasons, and mixtures thereof. In addition to the builder effect, the free acids typically also have the property of being an acidifying component and are thus also used as agents to set a lower and milder pH value. In particular, citric acid, succinic acid, glutaric acid, adipic acid, gluconic acid and arbitrary mixtures of these shall be mentioned here.

The use of citric acid and/or citrates in these agents has proven to be particularly advantageous for the cleaning and rinsing performance of agents described herein. Preferred are therefore cleaning agents, preferably dishwashing agents, particularly preferably automatic dishwashing agents, characterized in that the agent contains citric acid or a salt of citric acid, and the weight fraction of the citric acid or of the salt of citric acid is especially more than 10 wt. %, preferably more than 15 wt. %, and in particular between about 20 and about 40 wt. %.

Aminocarboxylic acids and/or the salts thereof are another significant class of builders. Particularly preferred representatives of this class are methylglycine diacetic acid (MGDA) or the salts thereof, and glutamine diacetic acid (GLDA) or the salts thereof or ethylenediamine diacetic acid (EDDS) or the salts thereof. Likewise suitable are iminodisuccinic acid (IDS) and iminodiacetic acid (IDA). The content of these aminocarboxylic acids or of the salts thereof can amount to between about 0.1 and about 15 wt. %, preferably between about 0.5 and about 10 wt. %, and in particular between 0.5 and 6 wt. %, for example. Aminocarboxylic acids and the salts thereof can be used together with the above-mentioned builders, in particular also with the phosphate-free builders.

As contemplated herein, preferably phosphate-free builders, in particular selected from citrate, GLDA and/or MGDA and optionally EDDS and/or IDS are used as builders.

Suitable builders are moreover polymeric polycarboxylates; for example, these are the alkali metal salts of polyacrylic acid or of polymethacrylic acid, for example those having a relative molar mass from about 500 to about 70000 g/mol, and polyaspartates and/or polyglutamates, for example, each either attached at the alpha position or linked to a side chain, or the copolymers thereof. Suitable polymers are in particular polyacrylates, which preferably have a molar mass from about 2000 to about 20000 g/mol. Due to the superior solubility thereof, short-chain polyacrylates having molar masses from about 2000 to about 10000 g/mol, and particularly preferably from about 3000 to about 5000 g/mol, may in turn be preferred from this group.

Also suitable are copolymeric polycarboxylates, in particular those of acrylic acid with methacrylic acid, and of acrylic acid or methacrylic acid with maleic acid.

The (co)polymeric polycarboxylates can be used either as a powder or as an aqueous solution. The content of (co) polymeric polycarboxylates in the cleaning agents, preferably dishwashing agents, in particular automatic dishwashing agents, is preferably about 0.5 to about 20 wt. %, and in particular about 3 to about 10 wt. %.

To improve water solubility, the polymers can also contain allyl sulfonic acids, such as allyloxybenzene sulfonic acid and methallyl sulfonic acid, as a monomer. Further preferred copolymers are those that contain acrolein and acrylic acid/acrylic acid salts or acrolein and vinylacetate as monomers.

The cleaning agents can in particular also comprise phosphonates as builders. The phosphonate compound used is preferably a hydroxyalkane phosphonate and/or aminoalkane phosphonate. Among the hydroxyalkane phosphonates, 1-hydroxyethane-1,1-diphosphonate (HEDP) is of particular importance. Possible preferable aminoalkane phosphonates include ethylenediaminetetramethylene phosphonate (EDTMP), diethylentriaminepentamethylene phosphonate (DTPMP) and the higher homologs thereof. Phosphonates are preferably present in the agents in amounts of about 0.1 to about 10 wt. %, and in particular in amounts of about 0.5 to about 8 wt. %, in each case based on the total weight of the cleaning agent.

Moreover, all compounds that are able to form complexes with alkaline earth ions can be used as builders.

The agents described herein may comprise surfactants, wherein the non-ionic, anionic, cationic and amphoteric surfactants are included in the group of surfactants.

All non-ionic surfactants known to a person skilled in the art may be used as non-ionic surfactants. Suitable non-ionic surfactants are, for example, alkyl glycosides of the general formula $RO(G)_x$, where R corresponds to a primary straight-chain or methyl-branched, in particular methyl-branched at the 2-position, aliphatic group having 8 to 22, preferably 12 to 18 carbon atoms, and G is the symbol that denotes a glycose unit having 5 or 6 carbon atoms, preferably glucose. The degree of oligomerization x, which indicates the distribution of monoglycosides and oligoglycosides, is an arbitrary number between 1 and 10; x is preferably 1.2 to 1.4.

Another class of non-ionic surfactants that can preferably be used, which can be used either as the sole non-ionic surfactant or in combination with other non-ionic surfactants, is alkoxylated, preferably ethoxylated or ethoxylated and propoxylated fatty acid alkyl esters, preferably having 1 to 4 carbon atoms in the alkyl chain.

Non-ionic surfactants of the amine oxide type, for example N-cocoalkyl-N—N-dimethylamine oxide and N-tallowalkyl-N,N-dihydroxyethylamine oxide, and of the fatty acid alkanolamide type may also be suitable. The quantity of these non-ionic surfactants is preferably no more than that of the ethoxylated fatty alcohols, in particular no more than half thereof.

Further suitable surfactants are polyhydroxyfatty acid amides, also known as PHFA.

Low-foaming non-ionic surfactants can be used as preferred surfactants. With particular preference, the cleaning agents, preferably dishwashing agents, in particular automatic dishwashing agents, contain non-ionic surfactants from the group of alkoxylated alcohols. Alkoxylated, advantageously ethoxylated, in particular primary alcohols having preferably 8 to 18 carbon atoms and on average 1 to 12 moles ethylene oxide (EO) per mole of alcohol, in which the alcohol residue can be linear or preferably methyl-branched at the 2-position, or can contain linear and methyl-branched residues in the mixture, such as those usually present in oxo alcohol groups, are preferably used as non-ionic surfactants. However, alcohol ethoxylates having linear groups of alcohols of native origin having 12 to 18 carbon atoms, for example of coconut, palm, tallow fatty or oleyl alcohol, and an average of 2 to 8 moles EO per mole of alcohol are particularly preferred. The preferred ethoxylated alcohols include, for example, $C_{12-14}$ alcohols having 3 EO or 4 EO, $C_{9-11}$ alcohol having 7 EO, $C_{13-15}$ alcohols having 3 EO, 5 EO, 7 EO, or 8 EO, $C_{12-18}$ alcohols having 3 EO, 5 EO, or 7 EO, and mixtures thereof, such as mixtures of $C_{12-14}$ alcohol having 3 EO and $C_{12-18}$ alcohol having 5 EO. The degrees of ethoxylation indicated represent statistical averages that can correspond to an integer or a fractional number for a specific product. Preferred alcohol ethoxylates exhibit a restricted distribution of homologs (narrow range ethoxylates, NRE). In addition to these non-ionic surfactants, fatty alcohols having more than 12 EO can also be used. Examples of these are tallow fatty alcohol having 14 EO, 25 EO, 30 EO, or 40 EO.

Non-ionic surfactants that have a melting point above room temperature are particularly preferred. Non-ionic surfactant(s) having a melting point above 20° C., preferably above 25° C., particularly preferably between about 25 and about 60° C., and in particular between about 26.6 and about 43.3° C., is/are particularly preferred.

Surfactants that are preferably to be used come from the groups of alkoxylated non-ionic surfactants, in particular ethoxylated primary alcohols.

Anionic surfactants can likewise be used as a component of cleaning agents, preferably dishwashing agents, in particular automatic dishwashing agents. These include in particular alkylbenzene sulfonates, (fatty) alkyl sulfates, (fatty) alkyl ether sulfates, and alkanesulfonates. The anionic surfactant content of the agents is usually 0 to about 10 wt. %.

Cationic and/or amphoteric surfactants can also be used instead of or in conjunction with the described surfactants. In cleaning agents, in particular dishwashing agents, preferably automatic dishwashing agents, the content of cationic and/or amphoteric surfactants is especially less than 6 wt. %, preferably less than 4 wt. %, especially particularly preferably less than 2 wt. %, and in particular less than 1 wt. %. Agents that contain no cationic or amphoteric surfactants are particularly preferred.

The group of polymers includes in particular polymers with washing or cleaning action, for example rinse polymers and/or polymers acting as softeners. In addition to non-ionic polymers, in general cationic, anionic, and amphoteric polymers can also be used in automatic dishwashing agents.

"Cationic polymers" within the meaning of the present disclosure are polymers that carry a positive charge in the polymer molecule. This charge can be implemented, for example, by way of (alkyl)ammonium groupings or other positively charged groups that are present in the polymer chain. Particularly preferred cationic polymers come from the groups of quaternized cellulose derivatives, polysiloxanes having quaternary groups, cationic guar derivatives, polymeric dimethyldiallylammonium salts and the copolymers thereof with esters and amides of acrylic acid and methacrylic acid, copolymers of vinylpyrrolidone with quaternized derivatives of dialkylaminoacrylate and -methacrylate, vinylpyrrolidone/methoimidazolinium chloride copolymers, quaternized polyvinyl alcohols, or the polymers described by the INCI names polyquaternium 2, polyquaternium 17, polyquaternium 18, and polyquaternium 27.

"Amphoteric polymers" within the meaning of the present disclosure further comprise negatively charged groups or monomer units, in addition to a positively charged group, in the polymer chain. These groups can be, for example, carboxylic acids, sulfonic acids or phosphonic acids.

Amphoteric polymers that are preferably used come from the group of alkylacrylamide/acrylic acid copolymers, alkylacrylamide/methacrylic acid copolymers, alkylacrylamide/methylmethacrylic acid copolymers, alkylacrylamide/acrylic acid/alkylaminoalkyl(meth)acrylic acid copolymers, alkylacrylamide/methacrylic acid/alkylaminoalkyl(meth)acrylic acid copolymers, alkylacrylamide/methylmethacrylic acid/alkylaminoalkyl(meth)acrylic acid copolymers, alkylacrylamide/alkyl methacrylate/alkylaminoethyl methacrylate/alkyl methacrylate copolymers, and copolymers of unsaturated carboxylic acids, cationically derivatized unsaturated carboxylic acids, and optionally further ionic or non-ionogenic monomers.

Preferred zwitterionic polymers come from the group of acrylamidoalkyltrialkylammonium chloride/acrylic acid copolymers and the alkali and ammonium salts thereof, acrylamidoalkyltrialkylammonium chloride/methacrylic acid copolymers and the alkali and ammonium salts thereof, and methacroylethylbetaine/methacrylate copolymers.

Cleaning agents, in particular dishwashing agents, preferably automatic dishwashing agents, preferably contain the above-mentioned cationic and/or amphoteric polymers in quantities between about 0.01 and about 10 wt. %, in each case based on the total weight of the automatic dishwashing agent. However, automatic dishwashing agents in which the weight fraction of cationic and/or amphoteric polymers is between about 0.01 and about 8 wt. %, especially between about 0.01 and about 6 wt. %, preferably between about 0.01 and about 4 wt. %, particularly preferably between about 0.01 and about 2 wt. %, and in particular between about 0.01 and about 1 wt. %, based in each case on the total weight of the automatic dishwashing agent, are preferred within the scope of the present application.

Bleaching agents can furthermore be used in the cleaning agents, preferably dishwashing agents, in particular automatic dishwashing agents. Among the compounds that serve as bleaching agents and yield $H_2O_2$ in water, sodium percarbonate, sodium perborate tetrahydrate, and sodium perborate monohydrate are of particular importance. Further usable bleaching agents are, for example, peroxypyrophosphates, citrate perhydrates, and peracid salts or peracids that yield $H_2O_2$, such as perbenzoates, peroxophthalates, diperazelaic acid, phthaloimino peracid, or diperdodecanedioic acid. All further inorganic or organic peroxy bleaching agents known from the prior art to a person skilled in the art may also be used.

Substances that release chlorine or bromine can also be used as bleaching agents. Among the suitable materials releasing chlorine or bromine, for example, heterocyclic N-bromamides and N-chloramides, such as trichloroisocyanuric acid, tribromoisocyanuric acid, dibromoisocyanuric acid, and/or dichloroisocyanuric acid (DICA), and/or the salts thereof with cations such as potassium and sodium can be considered. Hydantoin compounds, such as 1,3-dichloro-5,5-dimethylhydantoin, are likewise suitable.

Cleaning agents, preferably dishwashing agents, in particular automatic dishwashing agents that contain about 1 to about 35 wt. %, preferably about 2.5 to about 30 wt. %, particularly preferably about 3.5 to about 20 wt. %, and in particular about 5 to about 15 wt. % bleaching agent, preferably sodium percarbonate, are preferred.

The cleaning agents, preferably dishwashing agents, in particular automatic dishwashing agents can furthermore contain bleach catalysts. The usable bleach catalysts include, but are not limited to, the group of the bleach-boosting transition metal salts and transition metal complexes, preferably the Mn, Fe, Co, Ru or Mo complexes, particularly preferably from the group of the manganese and/or cobalt salts and/or complexes, in particular the cobalt (amine) complexes, the cobalt (acetate) complexes, the cobalt (carbonyl) complexes, the chlorides of cobalt or manganese, manganese sulfate and the complexes of manganese with 1,4,7-trimethyl-1,4,7-triazacyclononane (Mn3-TACN) or 1,2,4,7-tetramethyl-1,4,7-triazacyclononane (Mna-TACN).

Cleaning agents, preferably dishwashing agents, in particular automatic dishwashing agents that contain about 0.001 to about 1 wt. %, preferably about 0.01 to about 0.1 wt. % bleach catalyst, preferably an Mn complex, in particular a complex of manganese with 1,4,7-trimethyl-1,4,7-triazacyclononane ($Mn_3$-TACN) or 1,2,4,7-tetramethyl-1,4,7-triazacyclononane ($Mn_4$-TACN) are preferred.

In various embodiments of the disclosure, the cleaning agents, preferably dishwashing agents, in particular automatic dishwashing agents, additionally contain at least one bleach activator. Compounds that, under perhydrolysis conditions, yield aliphatic peroxocarboxylic acids having preferably 1 to 10 carbon atoms, in particular 2 to 4 carbon atoms, and/or optionally substituted perbenzoic acid, can be used as bleach activators. Out of all bleach activators known to a person skilled in the art from the prior art, polyacylated alkylenediamines, in particular tetra acetyl ethylene diamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoyl succinimide (NOSI), acylated phenolsulfonates, in particular n-nonanoyl or iso-nonanoyl oxybenzene sulfonate (n- or iso-NOBS), are particularly preferred. It is also possible to use combinations of conventional bleach activators. These bleach activators are preferably used in quantities of up to 10 wt. %, in particular about 0.1 wt. % to about 8 wt. %, particularly about 2 to about 8 wt. %, and particularly preferably about 2 to about 6 wt. %, based in each case on the total weight of the bleach activator-containing agent.

The agents of the present disclosure preferably contain at least one additional enzyme preparation or enzyme composition, which contains or more non-amylase and non-protease enzymes. Such enzymes include, without being limited thereto, lipases, cellulases, hemicellulases, mannanases, pectin-cleaving enzymes, tannanases, xylanases, xanthanases, β-glucosidases, carrageenanases, perhydrolases, oxidases, oxidoreductases, and the mixtures thereof. Preferred enzymes comprise in particular cellulases, lipases, hemicellulases, in particular pectinases, mannanases, β-glucanases, and the mixtures thereof. Particularly preferred are lipases. These enzymes are, in principle, of natural origin; proceeding from the natural molecules, improved variants are available for use in laundry detergents or cleaning agents and are used in correspondingly preferred fashion.

The information provided on quantities and formulation forms in connection with the amylases and proteases used apply, mutatis mutandis, also to all further above-described enzymes.

Glass corrosion inhibitors prevent the appearance of clouding, streaking, and scratching, but also iridescence of the glass surface of automatically cleaned glassware. Preferred glass corrosion inhibitors come from the group of magnesium and zinc salts and of the magnesium and zinc complexes. Within the scope of the present disclosure, the content of zinc salt in cleaning agents, preferably dishwashing agents, in particular automatic dishwashing agents, is especially between about 0.1 and about 5 wt. %, preferably between about 0.2 and about 4 wt. %, and in particular between about 0.4 and about 3 wt. %, or the content of zinc in oxidized formed (calculated as $Zn^{2+}$) is between about 0.01 and about 1 wt. %, especially between about 0.02 and about 0.5 wt. %, and in particular between about 0.04 and about 0.2 wt. %, in each case based on the total weight of the glass corrosion inhibitor-containing agent.

So as to facilitate the breakdown of prefabricated shaped bodies, it is possible to incorporate disintegration excipients, known as tablet disintegrants, into these agents in order to shorten breakdown times. Tablet disintegrants or breakdown accelerators are understood to mean excipients that ensure a rapid breakdown of tablets in water or other media, and the quick release of the active substances. Disintegration excipients can preferably be used in quantities from about 0.5 to about 10 wt. %, preferably about 3 to about 7 wt. %, and in particular about 4 to about 6 wt. %, in each case based on the total weight of the agent comprising the disintegration excipient.

Individual odorous substance compounds, such as synthetic products of the ester, ether, aldehyde, ketone, alcohol, and hydrocarbon types, can be used within the scope of the present disclosure as perfume oils or odorants. Preferably, however, mixtures of different odorants are used, which together produce an appealing odorous note. Such perfume oils can also contain natural odorous substance mixtures such as those accessible from plant sources, for example pine, citrus, jasmine, patchouli, rose, or ylang ylang oil.

Cleaning agents described herein, preferably dishwashing agents, in particular automatic dishwashing agents, can be formulated in a variety of ways. The agents can be present in solid or liquid presentation forms or as a combination of solid and liquid presentation forms. Suitable solid presentation forms are, in particular, powders, granules, extrudates, compactates, in particular tablets. The liquid presentation forms based on water and/or organic solvents can be present in thickened form, in the form of gels. Agents described herein can be formulated in the form of single-phase or multi-phase products.

Cleaning agents described herein, preferably dishwashing agents, in particular automatic dishwashing agents, are preferably preformulated as dosing units. These dosing units preferably comprise the quantity of substances with washing or cleaning action necessary for one cleaning cycle.

The cleaning agents described herein, preferably dishwashing agents, in particular automatic dishwashing agents, in particular the prefabricated dosing units, particularly preferably comprise a water-soluble wrapping.

The water-soluble wrapping is preferably formed of a water-soluble film material selected from the group consisting of polymers or polymer mixtures. The wrapping can be formed of one layer, or of two or more layers of the water-soluble film material. The water-soluble film material of the first layer and that of the further layers, if such are present, can be the same or different. Films that can be bonded and/or sealed, after they have been filled with the agent, to form packaging such as tubes or cushions, are particularly preferred.

It is preferable for the water-soluble wrapping to comprise polyvinyl alcohol or a polyvinyl alcohol copolymer. Water-soluble wrappings comprising polyvinyl alcohol or a polyvinyl alcohol copolymer exhibit good stability and sufficiently high water solubility, in particular cold water solubility.

It is particularly preferred when the prefabricated dosing units are formed by a water-soluble wrapping of an appropriate portioned amount of the composition as contemplated herein, which is to say the prefabricated dosing unit preferably comprises an agent as contemplated herein and a water-soluble wrapping/packaging.

The water-soluble wrappings/packagings are preferably thermoformed bodies or injection molded bodies.

The water-soluble containers/wrappings/packagings can also be produced by way of injection molding. Injection molding refers to the shaping of a molding compound in such a way that the compound present in an injection cylinder for more than one injection molding process undergoes plastic softening under the action of heat and, under pressure, flows through a nozzle into the cavity of a mold that was previously closed. The method is primarily employed for non-curable molding compounds, which solidify in the mold by cooling. Injection molding is a very economical modern method for producing objects shaped in a non-cutting operation and is particularly suitable for automated mass production. In practical operation, the thermoplastic molding compounds (powders, granules, cubes, pastes and the like) are heated until these liquefy (up to 180° C.), and then they are injected under high pressure (up to 140 MPa) into closed, two-piece, i.e., composed of the cavity (formerly female mold part) and the core (formerly male mold part), preferably water-cooled hollow molds, where they cool and solidify. Plunger and screw injection molding machines can be used.

These shaped bodies can likewise comprise one, two, three or more chambers and be filled with liquid and/or solid compositions, of which one of the compositions is one of the compositions as contemplated herein. For example, it is possible to close the chambers on the open side with either a second molded body or with one or more water-soluble films (in particular as described herein). In this way, the release of the compositions present in the chambers can be arbitrarily controlled based on the desired release point in time. It is possible to either release the entire agent at once (either directly at the beginning of the cleaning cycle or at a certain point in time during the course of the cleaning cycle) or, by varying the film composition, at certain points in time that are different from each other within the cycle of the dishwasher (for example, as a function of the temperature of the dishwater).

Suitable water-soluble films for producing the water-soluble wrapping are preferably based on a polyvinyl alcohol, or a polyvinyl alcohol copolymer, having a relative molar mass in the range from about 10,000 to about 1,000,000 $gmol^{-1}$, preferably from about 20,000 to about 500,000 $gmol^{-1}$, particularly preferably from about 30,000 to about 100,000 $gmol^{-1}$, and in particular from about 40,000 to about 80,000 $gmol^{-1}$.

The polyvinyl alcohol is typically produced by the hydrolysis of polyvinyl acetate since the direct synthesis pathway is not possible. The same applies to polyvinyl alcohol copolymers produced accordingly from polyvinyl acetate copolymers. It is preferred if at least one layer of the water-soluble wrapping comprises a polyvinyl alcohol having a degree of hydrolysis of about 70 to 100 mole %, preferably about 80 to about 90 mole %, particularly preferably about 81 to about 89 mole %, and in particular about 82 to about 88 mole %.

Additionally, a polymer selected from the group consisting of (meth)acrylic acid-containing (co)polymers, polyacrylamides, oxazoline polymers, polystyrene sulfonates, polyurethanes, polyesters, polyethers, polylactic acid or mixtures of the above polymers can be added to a polyvinyl alcohol-containing film material that is suitable for producing the water-soluble wrapping. A preferred additional polymer is polylactic acids.

In addition to vinyl alcohol, preferred polyvinyl alcohol copolymers comprise dicarboxylic acids as further monomers. Suitable dicarboxylic acids are itaconic acid, malonic acid, succinic acid and mixtures thereof, itaconic acid being preferred.

Likewise preferred polyvinyl alcohol copolymers include an ethylenically unsaturated carboxylic acid, the salt thereof, or the ester thereof, in addition to vinyl alcohol. In addition to vinyl alcohol, such polyvinyl alcohol copolymers particularly preferably comprise acrylic acid, methacrylic acid, acrylic acid esters, methacrylic acid esters or mixtures thereof.

It may be preferred for the film material to contain further additives. For example, the film material may contain plastizicers such as dipropylene glycol, ethylene glycol, diethylene glycol, propylene glycol, glycerol, sorbitol, mannitol or mixtures thereof. Examples of further additives include release aids, fillers, cross-linking agents, surfactants, antioxidants, UV absorbers, anti-blocking agents, non-stick agents or mixtures thereof.

Suitable water-soluble films for use in the water-soluble wrappings of the water-soluble packagings as contemplated herein are films sold by MonoSol LLC, for example, by the designation M8630, C8400 or M8900. Other suitable films include films by the designation Solublon® PT, Solublon® GA, Solublon® KC or Solublon® KL from Aicello Chemical Europe GmbH, or the VF-HP films from Kuraray.

A further object of the disclosure is also the corresponding use of the agents described herein. The disclosure also relates to a dishwashing method, in particular an automatic dishwashing method, in which an agent as contemplated herein is used. A further object of the present application is therefore moreover a method for cleaning dishes in an automatic dishwasher, in which the agent is dispensed into the interior of an automatic dishwasher while a dishwashing program is being executed, before the main washing cycle begins, or in the course of the main washing cycle. Dispensing or introduction of the agent into the interior of the automatic dishwasher can take place manually, but preferably the agent is dispensed into the interior of the automatic dishwasher by means of the dosing chamber. In various embodiments of the disclosure, the (washing) temperature in such dishwashing methods is preferably 50° C. or lower, particularly preferably 45° C. or lower, still more preferably 40° C. or lower.

Finally, the disclosure also relates to the use of the enzyme combinations described herein for improving the cleaning performance, and in particular the cleaning performance when it comes to enzyme-sensitive soiling, of a cleaning agent, in particular a dishwashing agent, especially an automatic dishwashing agent. All enzyme combinations described as specific embodiments in the context of the cleaning agents disclosed herein can also be employed in the described methods and uses.

A typical basic formula for a preferably usable automatic dishwashing agent, for example in tablet form, comprises the following substances:

| | |
|---|---|
| sodium tripolyphosphate | about 20 to about 50 wt. % |
| sodium carbonate | about 10 to about 30 wt. % |
| sodium percarbonate | about 5 to about 18 wt. % |
| bleach activator | about 0.5 to about 5 wt. % |
| bleach catalyst | about 0.01 to about 1 wt. % |
| sulfopolymer | about 2.5 to about 15 wt. % |
| polycarboxylate | about 0.1 to about 10 wt. % |
| non-ionic surfactant | about 0.5 to about 10 wt. % |
| phosphonate | about 0.5 to about 5 wt. % |
| proteases | about 0.1 to about 5 wt. % |
| amylases | about 0.1 to about 5 wt. % |

wherein the information in wt. % in each case is based on the total agent. Instead of a portion of the tripolyphosphate, it is in particular possible to also use about 10 to about 50 wt. % citrate or MGDA or GLDA or EDDS or mixtures of two or three of these substances in the formula.

EXAMPLES

Example 1: Improving the Amylase Performance During Automatic Dishwashing

TABLE 1

Composition of the automatic dishwashing agent

| | Base |
|---|---|
| Tripolyphosphate (wt/%) | 35.9 |
| Sodium carbonate (wt/%) | 12.2 |
| Phosphonate (wt/%) | 2.4 |
| Sulfonic acid group-containing polymer (wt/%) | 7.9 |
| Polyacrylate (wt/%) | 4.6 |
| Non-ionic surfactants (wt/%) | 6.1 |
| Percarbonate (wt/%) | 14.6 |
| TAED (wt/%) | 2.3 |
| Bleach catalyst (wt/%) | 1.0 |
| Polycarboxylate (wt/%) | 1.5 |
| Sodium silicate/polycarboxylate (wt/%) | 3.9 |
| Zinc acetate (wt/%) | 0.2 |
| Remainder (perfume, dyes, protease or protease mixture etc.) (wt/%) | to make up 100 |

Spaghetti Soiling Cleaning Performance

In a Bosch automatic dishwasher, china plates containing soiling of spaghetti were washed at 40° C. ("Normal" program) and 21° dH water hardness using a solid dishwashing tablet (20 g; for composition, see Table 1) comprising two individual amylases (comparative experiments V1, V2) or amylase combinations (M1).

The cleaning performance was visually determined according to IKW (German Cosmetic, Toiletry, Perfumery and Detergent Association) after each washing cycle (evaluation from 1 to 10; the higher the value, the better the performance; differences of at least 1 are significant). The results for the tested formulas are listed in Table 2 as arithmetic means from 3 determinations.

Either 50 mg/job amylase 1 (V1) or 5 mg/job or amylase 2 (V2) or the mixture thereof (M1, 25 mg/job amylase 1 and 2.5 mg/job amylase 2) (in each case based on the amount of the enzyme protein) was added to the formulation according to Table 1.

TABLE 2

Spaghetti cleaning performance

| Amylase/Amylase combination | Spaghetti |
|---|---|
| M1: | 3.8 |
| V1: | 2.8 |
| V2: | 2.2 |

V1: base + 50 mg/job 1st amylase (enzyme according to SEQ ID NO. 1 comprising the amino acid substitutions M202L, S255N and R172Q)
V2: base + 5 mg/job 2nd amylase based on active protein (Stainzyme Plus ™)
M1: base + mixture of the enzymes according to V1 and V2 (25 mg/job amylase 1 and 2.5 mg/job amylase 2, in each case based on the amount of active protein)

It is clearly apparent from Table 2 that the combination of the two different amylases results in a considerable improvement of the cleaning performance (M1).

Example 2: Cleaning Performance in Phosphate-Free Dishwashing Agents

China plates containing soiling of tea (Assam, BOP, Lipton), ground meat, egg yolk, spaghetti, starch and créme brulee were washed in a Miele GSL automatic dishwasher at 50° C. ("Normal" program) and 21° dH, and in a Bosch SMS68M62 automatic dishwasher at 40° C. ("Gentle 40" program) and 21° dH, using a solid dishwashing tablet. Various enzymes were added to the formulation according to Table 3 in the indicated amounts (mg active protein/job) (V1 to V6: comparative experiments; E1 to E3: as contemplated herein):

| | mg protease 1 | mg protease 2 | mg amylase 1 | mg amylase 2 |
|---|---|---|---|---|
| V1 | 50 | 25 | 0 | 5 |
| V2 | 80 | 0 | 0 | 5 |
| V3 | 0 | 80 | 0 | 5 |
| V4 | 80 | 0 | 50 | 0 |
| V5 | 0 | 80 | 50 | 0 |
| V6 | 50 | 25 | 50 | 0 |
| E1 | 80 | 0 | 25 | 2.5 |
| E2 | 50 | 25 | 25 | 2.5 |
| E3 | 0 | 80 | 25 | 2.5 |

Protease 1: enzyme according to SEQ ID NO. 5
Protease 2: enzyme according to SEQ ID NO. 6
Amylase 1: enzyme according to SEQ ID NO. 1 comprising the amino acid substitutions M202L, S255N and R172Q
Amylase 2: Stainzyme Plus ™

TABLE 3

Composition of the automatic dishwashing agent in wt. % active substance

| | Base |
|---|---|
| Na citrate | 20 |
| MGDA | 16 |
| Phosphonate | 5 |
| Soda | 15 |
| Na percarbonate | 15 |
| Sulfonic acid group-containing polymer | 8 |
| Polyacrylate | 0.5 |
| Non-ionic surfactants | 7 |
| TAED | 3 |
| Bleach catalyst | 1 |
| Zinc acetate | 0.2 |
| Na sulfate | 0.5 |
| PEG 4000 | 0.5 |
| Remainder (pH setting agent, perfume, dyes, etc.) | to make up 100 |

The cleaning performance was visually determined according to IKW (German Cosmetic, Toiletry, Perfumery and Detergent Association) (evaluation from 1 to 10; the higher the value, the better the performance; differences of at least 1 are significant). The results for the tested formulas are listed in Table 4 as arithmetic means. Higher values indicate better cleaning performance.

TABLE 4

Sum of the cleaning performance regarding various soiling types:

| Enzyme combinations (50° C.) | |
|---|---|
| V1 | 65.1 |
| V2 | 62.3 |
| V3 | 61.3 |
| V4 | 66.2 |
| V5 | 66.2 |
| V6 | 67.1 |
| E1 | 68.6 |
| E2 | 70.5 |
| E3 | 68.5 |

| Enzyme combinations (40° C.) | |
|---|---|
| V1 | 63.6 |
| V2 | 62.5 |
| V3 | 59 |
| V4 | 65 |
| V5 | 63.5 |
| V6 | 66.3 |
| E1 | 64.4 |
| E2 | 66.2 |
| E3 | 63.9 |

It is clearly apparent from Table 4 that the combinations as contemplated herein result in an increase in the cleaning performance.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A cleaning agent for hard surfaces, comprising:

at least one first amylase including an amino acid sequence that is at least 80% identical to the amino acid sequence indicated in SEQ ID NO. 1 over the total length thereof, wherein the first amylase is an α-amylase from *Bacillus* sp. No. 707 or a functional fragment or a variant thereof; and at least one second amylase including an amino acid sequence that is at least 80% identical to the amino acid sequence indicated in SEQ ID NO. 2 over the total length thereof, wherein the second amylase is an AA560 α-amylase from *Bacillus* sp. or a functional fragment or a variant thereof, wherein the first amylase and the second amylase are present in a weight ratio of 10:1, respectively.

2. The cleaning agent according to claim 1, wherein the first amylase has at least one amino acid substitution at one of positions 172, 202, 208, 255 and 261 in the count according to SEQ ID NO. 1.

3. The cleaning agent according to claim 1 wherein the second amylase has at least one amino acid substitution at one of positions 9, 26, 30, 33, 82, 37, 106, 118, 128, 133, 149, 150, 160, 178, 182, 186, 193, 195, 202, 203, 214, 231, 256, 257, 258, 269, 270, 272, 283, 295, 296, 298, 299, 303, 304, 305, 311, 314, 315, 318, 319, 320, 323, 339, 345, 361, 378, 383, 419, 421, 437, 441, 444, 445, 446, 447, 450, 458, 461, 471, 482 and 484 and/or one of the deletions D183* and G184* in the count according to SEQ ID NO. 2.

4. The cleaning agent according to claim 3, wherein the second amylase, in the count according to SEQ ID NO. 2, includes amino acid substitutions at three or more of positions 9, 26, 149, 182, 186, 202, 257, 295, 299, 323, 339 and 345.

5. The cleaning agent according to claim 3, wherein the second amylase includes the following amino acid substitutions and/or deletions in the count according to SEQ ID NO. 2:

(i) M9L+M323T;

(ii) M9L+M202L/T/V/I+M323T;

(iii) M9L+N195F+M202L/T/V/I+M323T;

(iv) M9L+R118K+D183*+G184*+R320K+M323T+R458K;

(v) M9L+R118K+D183*+G184*+M202L/T/V/I+R320K+M323T+R458K;

(vi) M9L+G149A+G182T+G186A+M202L+T257I+Y295F+N299Y+M323T+A339S+E345R;

(vii) M9L+G149A+G182T+G186A+M202I+T257I+Y295F+N299Y+M323T+A339S+E345R;

(viii) M9L+R118K+G149A+G182T+D183*+G184*+G186A+M202L+T257I+Y295F+N299Y+R320K+M323T+A339S+E345R+R458K;

(ix) M9L+R118K+G149A+G182T+D183*+G184*+G186A+N195F+M202L+T257I+Y295F+N299Y+R320K+M323T+A339S+E345R+R458K;

(x) M9L+R118K+G149A+G182T+D183*+G184*+G186A+M202I+T257I+Y295F+N299Y+R320K+M323T+A339S+E345R+R458K;
(xi) M9L+R118K+D183*+D184*+N195F+M202L+R320K+M323T+R458K;
(xii) M9L+R118K+D183*+D184*+N195F+M202T+R320K+M323T+R458K;
(xiii) M9L+R118K+D183*+D184*+N195F+M202I+R320K+M323T+R458K;
(xiv) M9L+R118K+D183*+D184*+N195F+M202V+R320K+M323T+R458K;
(xv) M9L+R118K+N150H+D183*+D184*+N195F+M202L+V214T+R320K+M323T+R458K; or
(xvi) M9L+R118K+D183*+D184*+N195F+M202L+V214T+R320K+M323T+E345N+R458K.

6. The cleaning agent according to claim 1, wherein the cleaning agent furthermore comprises at least one protease.

7. The cleaning agent according to claim 6, wherein the at least one protease:

(a) comprises a subtilisin 309 from *Bacillus lentus* or a functional fragment or a variant thereof, comprises an amino acid sequence that is at least 80% identical to the amino acid sequence indicated in SEQ ID NO. 3 over the total length thereof, and has at least one amino acid substitution at one of positions 9, 15, 66, 212 and 239 in the count according to SEQ ID NO. 3; and/or (b) comprises a subtilisin 309 from *Bacillus lentus* or a functional fragment or a variant thereof, comprises an amino acid sequence that is at least 80% identical to the amino acid sequence indicated in SEQ ID NO. 3 over the total length thereof, and has an amino acid substitution at position 99 and an insertion of one amino acid between the amino acids at positions 99 and 100 in the count according to SEQ ID NO. 3; and/or (c) comprises an alkaline protease from *Bacillus lentus* DSM 5483 or a functional fragment or a variant thereof, includes an amino acid sequence that is at least 80% identical to the amino acid sequence indicated in SEQ ID NO. 4 over the total length thereof; and/or (d) comprises an amino acid sequence according to one of SEQ ID NOs: 5 to 8.

8. The cleaning agent according to claim 7, wherein the at least one protease comprises two or more proteases.

9. The cleaning agent according to claim 1, wherein the weight fraction of each of the amylases, based on the corresponding active protein, in the total weight of the agent is from about $1\times10^{-8}$ to about 5 wt. %.

10. The cleaning agent according to claim 1, comprising at least one further component selected from the group consisting of builders, surfactants, polymers, bleaching agents, bleach catalysts, bleach activators, non-protease and non-amylase enzymes, corrosion inhibitors, glass corrosion inhibitors, disintegrants, odorants and perfume carriers.

11. The cleaning agent according to claim 1, wherein the cleaning agent is an automatic dishwashing agent, and the (1) automatic dishwashing agent is present in solid form; and/or (2) the automatic dishwashing agent is present in preportioned form; and/or (3) the automatic dishwashing agent comprises multiple compositions that are physically separated from each other.

12. Method for cleaning dishes in an automatic dishwasher, wherein a cleaning agent according to claim 1 is dispensed into the interior of an automatic dishwasher while a dishwashing program is being executed, before the main washing cycle begins, or in the course of the main washing cycle.

13. The cleaning agent according to claim 2, wherein the first amylase has at least one amino acid substitution selected from the group consisting of M202L, S255N and R172Q.

14. The cleaning agent according to claim 4, wherein the second amylase, in the count according to SEQ ID NO. 2, includes amino acid substitutions and/or deletions at positions 118, 183, 184, 195, 320 and 458.

15. The cleaning agent according to claim 14, wherein the second amylase, in the count according to SEQ ID NO. 2, has one or more of the following substitutions and/or deletions: R118K, D183*, G184*, N195F, R320K and/or R458K.

16. A cleaning agent for hard surfaces, comprising:

at least one first amylase including an amino acid sequence that is at least 80% identical to the amino acid sequence indicated in SEQ ID NO. 1 over the total length thereof, wherein the first amylase is an α-amylase from *Bacillus* sp. No. 707 or a functional fragment or a variant thereof;

at least one second amylase including an amino acid sequence that is at least 80% identical to the amino acid sequence indicated in SEQ ID NO. 2 over the total length thereof, wherein the second amylase is an AA560 α-amylase from *Bacillus* sp. or a functional fragment or a variant thereof, a first protease comprising a subtilisin 309 from *Bacillus lentus* or a functional fragment or a variant thereof, comprising an amino acid sequence that is at least 80% identical to the amino acid sequence indicated in SEQ ID NO. 5 over the total length thereof; and a second protease comprising a subtilisin 309 from *Bacillus lentus* or a functional fragment or a variant thereof, comprising an amino acid sequence that is at least 80% identical to the amino acid sequence indicated in SEQ ID NO. 6 over the total length thereof, wherein the first amylase and the second amylase are present in a weight ratio of 10:1, respectively.

17. The cleaning agent according to claim 16, wherein the first amylase has an amino acid substitution at M202L, S255N and R172Q.

18. The cleaning agent according to claim 17, wherein the second amylase has at least one amino acid substitution at one of positions 9, 26, 30, 33, 82, 37, 106, 118, 128, 133, 149, 150, 160, 178, 182, 186, 193, 195, 202, 203, 214, 231, 256, 257, 258, 269, 270, 272, 283, 295, 296, 298, 299, 303, 304, 305, 311, 314, 315, 318, 319, 320, 323, 339, 345, 361, 378, 383, 419, 421, 437, 441, 444, 445, 446, 447, 450, 458, 461, 471, 482 and 484 and/or one of the deletions D183* and G184* in the count according to SEQ ID NO. 2.

19. The cleaning agent according to claim 16, wherein the second amylase has at least one amino acid substitution at one of positions 9, 26, 30, 33, 82, 37, 106, 118, 128, 133, 149, 150, 160, 178, 182, 186, 193, 195, 202, 203, 214, 231, 256, 257, 258, 269, 270, 272, 283, 295, 296, 298, 299, 303, 304, 305, 311, 314, 315, 318, 319, 320, 323, 339, 345, 361, 378, 383, 419, 421, 437, 441, 444, 445, 446, 447, 450, 458, 461, 471, 482 and 484 and/or one of the deletions D183* and G184* in the count according to SEQ ID NO. 2.

20. An automatic dishwashing agent comprising:

at least one first amylase including an amino acid sequence that is at least 80% identical to the amino acid sequence indicated in SEQ ID NO. 1 over the total length thereof, wherein the first amylase is an α-amylase from *Bacillus* sp. No. 707 or a functional fragment or a variant thereof;

at least one second amylase including an amino acid sequence that is at least 80% identical to the amino acid sequence indicated in SEQ ID NO. 2 over the total length thereof, wherein the second amylase is an AA560 α-amylase from *Bacillus* sp. or a functional fragment or a variant thereof, a first protease comprising a subtilisin 309 from *Bacillus lentus* or a functional fragment or a variant thereof, comprising an amino acid sequence that is at least 80% identical to the amino acid sequence indicated in SEQ ID NO. 5 over the total length thereof; and a second protease comprising a subtilisin 309 from *Bacillus lentus* or a functional fragment or a variant thereof, comprising an amino acid sequence that is at least 80% identical to the amino acid sequence indicated in SEQ ID NO. 6 over the total length thereof, wherein the first amylase and the second amylase are present in a weight ratio of 10:1, respectively, wherein the first protease and the second protease are present in a weight ratio of about 2:1, respectively, wherein the first amylase has an amino acid substitution at M202L, S255N and R172Q, wherein the second amylase includes the following amino acid substitutions and/or deletions in the count according to SEQ ID NO. 2:

(i) M9L+M323T;

(ii) M9L+M202L/T/V/I+M323T;

(iii) M9L+N195F+M202L/T/V/I+M323T;

(iv) M9L+R118K+D183*+G184*+R320K+M323T+R458K;

(v) M9L+R118K+D183*+G184*+M202L/T/V/I+R320K+M323T+R458K;

(vi) M9L+G149A+G182T+G186A+M202L+T257I+Y295F+N299Y+M323T+A339S+E345R;

(vii) M9L+G149A+G182T+G186A+M202I+T257I+Y295F+N299Y+M323T+A339S+E345R;

(viii) M9L+R118K+G149A+G182T+D183*+G184*+G186A+M202L+T257I+Y295F+N299Y+R320K+M323T+A339S+E345R+R458K;

(ix) M9L+R118K+G149A+G182T+D183*+G184*+G186A+N195F+M202L+T257I+Y295F+N299Y+R320K+M323T+A339S+E345R+R458K;

(x) M9L+R118K+G149A+G182T+D183*+G184*+G186A+M202I+T257I+Y295F+N299Y+R320K+M323T+A339S+E345R+R458K;

(xi) M9L+R118K+D183*+D184*+N195F+M202L+R320K+M323T+R458K;

(xii) M9L+R118K+D183*+D184*+N195F+M202T+R320K+M323T+R458K;

(xiii) M9L+R118K+D183*+D184*+N195F+M202I+R320K+M323T+R458K;

(xiv) M9L+R118K+D183*+D184*+N195F+M202V+R320K+M323T+R458K;

(xv) M9L+R118K+N150H+D183*+D184*+N195F+M202L+V214T+R320K+M323T+R458K; or (xvi) M9L+R118K+D183*+D184*+N195F+M202L+V214T+R320K+M323T+E345N+R458K.

* * * * *

SEQUENCE LISTING

```
<160> NUMBER OF SEQ ID NOS: 8

<210> SEQ ID NO 1
<211> LENGTH: 485
<212> TYPE: PRT
<213> ORGANISM: Bacillus sp. No.707

<400> SEQUENCE: 1

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
```

-continued

```
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485


<210> SEQ ID NO 2
<211> LENGTH: 485
<212> TYPE: PRT
<213> ORGANISM: Bacillus sp.

<400> SEQUENCE: 2

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80
```

-continued

```
Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485
```

-continued

```
<210> SEQ ID NO 3
<211> LENGTH: 269
<212> TYPE: PRT
<213> ORGANISM: Bacillus lentus

<400> SEQUENCE: 3

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 4
<211> LENGTH: 269
<212> TYPE: PRT
<213> ORGANISM: Bacillus lentus

<400> SEQUENCE: 4

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
```

-continued

```
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 5
<211> LENGTH: 269
<212> TYPE: PRT
<213> ORGANISM: Artificial
<220> FEATURE:
<223> OTHER INFORMATION: Optimized B. lentus subtilisin 309 variant

<400> SEQUENCE: 5

Ala Gln Ser Val Pro Trp Gly Ile Arg Arg Val Gln Ala Pro Thr Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Ala Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
```

-continued

```
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asp Gly Thr Ser Met Ala Thr Pro His Val Ala Gly Ala
    210                 215                 220

Ala Ala Leu Val Lys Gln Lys Asn Pro Ser Trp Ser Asn Val Arg Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 6
<211> LENGTH: 270
<212> TYPE: PRT
<213> ORGANISM: Artificial
<220> FEATURE:
<223> OTHER INFORMATION: Optimized B. lentus subtilisin 309 variant

<400> SEQUENCE: 6

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ala Asp Gly Ser Val Ser Ser Ile Ala Gln Gly Leu Glu Trp
            100                 105                 110

Ala Gly Asn Asn Gly Met His Val Ala Asn Leu Ser Leu Gly Ser Pro
        115                 120                 125

Ser Pro Ser Ala Thr Leu Glu Gln Ala Val Asn Ser Ala Thr Ser Arg
    130                 135                 140

Gly Val Leu Val Val Ala Ala Ser Gly Asn Ser Gly Ala Gly Ser Ile
145                 150                 155                 160

Ser Tyr Pro Ala Arg Tyr Ala Asn Ala Met Ala Val Gly Ala Thr Asp
                165                 170                 175

Gln Asn Asn Asn Arg Ala Ser Phe Ser Gln Tyr Gly Ala Gly Leu Asp
            180                 185                 190

Ile Val Ala Pro Gly Val Asn Val Gln Ser Thr Tyr Pro Gly Ser Thr
        195                 200                 205

Tyr Ala Ser Leu Asn Gly Thr Ser Met Ala Thr Pro His Val Ala Gly
    210                 215                 220

Ala Ala Ala Leu Val Lys Gln Lys Asn Pro Ser Trp Ser Asn Val Gln
225                 230                 235                 240

Ile Arg Asn His Leu Lys Asn Thr Ala Thr Ser Leu Gly Ser Thr Asn
                245                 250                 255

Leu Tyr Gly Ser Gly Leu Val Asn Ala Glu Ala Ala Thr Arg
```

-continued

```
            260                 265                 270


<210> SEQ ID NO 7
<211> LENGTH: 269
<212> TYPE: PRT
<213> ORGANISM: Artificial
<220> FEATURE:
<223> OTHER INFORMATION: Optimized B. lentus alkaline protease variant

<400> SEQUENCE: 7

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Glu Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 8
<211> LENGTH: 269
<212> TYPE: PRT
<213> ORGANISM: Artificial
<220> FEATURE:
<223> OTHER INFORMATION: Optimized B. lentus alkaline protease variant

<400> SEQUENCE: 8

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30
```

-continued

```
Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Glu Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```